US005789231A

United States Patent [19]

Spijkers et al.

[11] Patent Number: 5,789,231
[45] Date of Patent: Aug. 4, 1998

[54] MAREK'S DISEASE VACCINE

[75] Inventors: Hubertine E. M. Spijkers; Jacob J. Louwerens, both of Weesp, Netherlands

[73] Assignee: American Cyanamid Company, Madison, N.J.

[21] Appl. No.: 662,450

[22] Filed: Jun. 10, 1996

[30] Foreign Application Priority Data

Jun. 12, 1995 [EP] European Pat. Off. .............. 95201540

[51] Int. Cl.$^6$ .............................. C12N 7/00; C12N 7/04; C12N 7/08; C12N 1/00

[52] U.S. Cl. ....................... 435/235.1; 435/243; 435/245; 435/237; 435/239; 424/229.1

[58] Field of Search .................... 424/229.1; 435/240.23, 435/240.21, 240.25, 235.1, 243, 245, 237, 239

[56] References Cited

U.S. PATENT DOCUMENTS 4,071,618 1/1978 Konobe et al. .

4,673,572 6/1987 De Boer .................................... 424/89

FOREIGN PATENT DOCUMENTS 015074 10/1985 European Pat. Off. .

OTHER PUBLICATIONS

Schnitzlein, et al.: Replication of infectious laryngotracheitis . . . : Avian Diseases:39:pp. 528–531, 1995.
Schnitzlein, et al. Propagation of onfectious laryngotracheitis . . . : Avian Diseases: 38:pp. 211–217, 1994.
Cowan, et al.: The propagation of avian viruses in a continuous cell line . . . : Avian Diseases: 32; pp. 282–297, 1988.
Fenner et al., (1987), "Veterinary Virology", pp. 273–277.
Cowen et al., "The Propagation of Avian Viruses in a Continuous Cell Line (QT35) of Japanese Quail Origin", (1988), Avian Diseases 32, pp. 282–297.
Ben–Nathan et al.–(1990) Adv. in Biotech. Processes 14, pp. 347–365.
B.R. Cho, "A Simple In Vitro Differentiation Between Turkey Herpesvirus and Marek's Disease Virus", Avian Diseases 25 (4), pp. 839–846.

*Primary Examiner*—Lynette F. Smith

*Assistant Examiner*—Brett Nelson

*Attorney, Agent, or Firm*—Stevens, Davis, Miller & Mosher, L.L.P.

[57] ABSTRACT

The present invention is concerned with Marek's Disease Virus of serotype 1 adapted for growth on an avian cell line. A preferred cell line for adaption of this virus is the quail cell line QT-35. These adapted viruses can be grown on the avian cell line in order to obtain virus material for the preparation of vaccines.

5 Claims, 1 Drawing Sheet

MAREK'S DISEASE VACCINE

The present invention is concerned with a novel Marek's Disease Virus [MDV] vaccine strain, with a method for growing said virus and with a vaccine containing said virus.

Marek's disease virus can cause severe economic losses in poultry industry. Most severe are losses caused by serotype 1 wild-type viruses. Serotypes 2 and 3 also can be found in the field. The serotype 1 virus is an oncogenic strain, serotype 2 is non-oncogenic and serotype 3 is a herpes virus of turkeys (HVT). The different types have a high degree of similarity with respect to their antigenic properties, however, they differ with respect to their clinical significance.

In order to reduce economic losses by Marek's disease [MD], vaccines have been developed. Vaccines against MD have been derived from all of the above 3 serotypes. The present invention is concerned with a serotype 1 vaccine virus.

Serotype 1 MD viruses are usually strongly cell-associated in vitro. As a substrate for growth of this virus chicken embryo fibroblasts (CEF) are generally used. The use of CEF has some disadvantages. CEF are harvested from embryonated specific pathogen-free chicken eggs. In order to obtain sufficient cells large numbers of these expensive eggs are required and harvesting of the cells is time and labor consuming. The quality of CEF is variable and the process of harvesting requires a large number of a-septic handlings, resulting in high risks for contamination.

In the prior art several cell types have been described which can be used to grow MDV, for example primary fibroblast cultures obtained from turkey, goose, pigeon, pheasant, bobwhite and Japanese quail embryos. However, it would be most convenient to have a continuous cell line available for vaccine virus production.

The advantage of the use of a continuous cell line for production purposes is that samples of cells easily can be obtained from a previously established and fully controlled cell bank stored in, for example, liquid nitrogen. The quality of continuous cell lines is more constant than the quality of CEF and because the use of a continuous cell line is less laborious and less a-septic handlings have to be carried out, risks for contamination are lower.

Surprisingly, it has now been found that MDV serotype 1 can be adapted to growth on a continuous avian cell line. More in particular, use can be made of a quail cell line, such as the QT35 (Japanese quail tumor) cell line. The adapted virus can be grown on avian cell lines with yields high enough for economical production of vaccine. Experimental evidence shows that the adapted vaccine virus, propagated for example on QT35 cells is still able to induce protective immunity against MD in chickens. This adapted Marek's disease virus strain can be derived from well-known attenuated MDV strains, such as strain Rispens, CVI988.

This finding is surprising because it is known from the prior art (Cho, 1981, Avian diseases 25: 839–846) that serotype 1 viruses can be distinguished from serotype 3 viruses by a test in which the QT35 cell line is used as substrate for the viruses. Inoculation of serotype 3 virus would result in a distinct cytopathologic effect (c.p.e.) whereas after inoculation of the serotype 1 viruses no c.p.e. was detected, suggesting insufficient growth of these viruses on QT35 cells.

A culture of a continuous or established cell line can be grown without restrictions and can undergo an unlimited number of passages. This is in contrast with primary cell cultures which can be maintained for only a few passages.

Primary cell cultures are in vitro cultures of cells directly isolated from tissues such as liver, kidney, spleen, eggs. If the tissue from which the primary cells are obtained is contaminated with micro-organisms, there is a high probability that the cells will also be contaminated. Even very stringent housing conditions and extensive control of animals from which the cells or the eggs are obtained can not garantee that the cells are free from extraneous agents.

The use of an established cell line opens the possibility to prepare a cell bank. This is a large batch of cells which is filled in aliquots and stored in, for example, liquid nitrogen. The batch is tested extensively for absence of extraneous agents. The risk that the use of this cell bank would be a source of contamination of products is extremely small. Hence, the use of an established cell line clearly lowers the risk for contamination of the end product, in comparison to the use of primary cell cultures.

Another advantage of established cell lines from a cell bank, over primary cell cultures is the constant and reliable quality. Each aliquot of the cell line has the same quality. In contrast, the quality of primary cells depends on the condition of the animal or the egg from which the tissue was obtained.

DETAILED DESCRIPTION OF THE INVENTION

Figure 1:
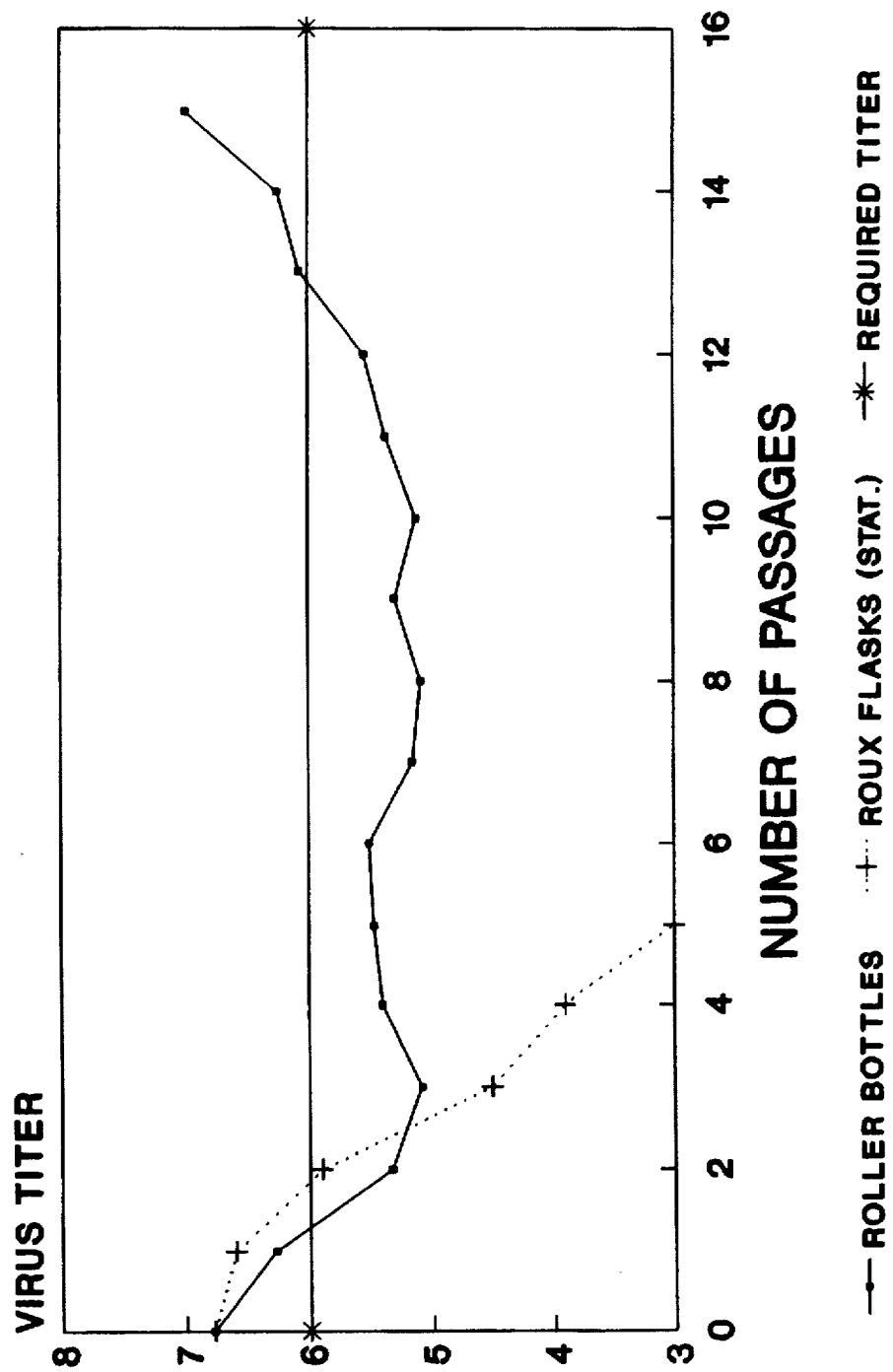
FIG. 1 is a graphic representation of virus titer versus the number of passages in which the strain CVI-988 were cultured in Roux flasks on QT-35 cells in comparison with passaging the same virus in roller bottles on QT-35 cells.

In order to prepare adapted MDV, several passages were made with strain CVI988 on QT35 cells. During the first passages the virus was found to multiply to a very low extent. Upon application of a high multiplicity of infection in roller bottles some c.p.e. could be obtained. It was found that after a number of successive passages in roller bottles virus yields increase. Instead, during passages in stationary cultures (Roux flasks, 75 cm$^2$ per bottle) the virus dissappeared. In FIG. 1 the virus titer (expressed as $^{10}$log TCID$_{50}$ per $3.10^7$ cells) is represented after each passage during the adaptation of MDV strain CVI988 to QT35 cells in roller bottles or Roux flasks, respectively. After a sufficiently high number of passages in roller bottles the virus yields are thus high that a profitable production system is obtained. It can be seen that the virus titer increased after the 12$^{th}$ passage in roller bottles.

A following adaptation experiment was performed. In this experiment also titers increased during passaging. In order to illustrate the adaptation effect, at the second passage a TCID$_{50}$ titer of $10^{6.63}$ per $3.10^7$ cells was generated and the harvested virus from one roller bottle could be used to inoculate 5 roller bottles with QT35 cells. At passage 19 a titer of $10^{7.02}$ per $3.10^7$ cells was generated, high enough to inoculate 50 roller bottles with the harvest of one roller bottle.

During the adaptation experiment several attempts were done to increase virus titers. In certain cases the harvested virus was not inoculated upon QT35 monolayers, but was mixed with a freshly prepared suspension of QT35 cells and subsequently seeded in roller bottles. In other cases the harvested virus was not even mixed with fresh cells but the harvest was simply subcultured in empty roller bottles. The manipulations resulted in harvested cultures with virus titers sufficiently high to continue passaging. For the propagation on QT35 cells a high multiplicity of infection is crucial. To this end high virus titers are required. After harvesting virus was always directly passaged further and no freezing step was included. In order to screen the harvested virus suspension for virus content, an immunofluorescence assay was performed.

The development of the QT35 cell line has been described by Moscovici et al. (1977 Cell 11: 95–103). The QT35 cell line was established from a methylcholanthrene-induced fibrosarcoma of Japanese quail. Samples of this cell line have been deposited at ATCC (Rockville, Md., USA) under No. CRL 10967.

QT35 cells can be grown by various culture methods suitable for anchorage dependent cells. For example, the cells can be grown in roller bottles, in cell cubes and on microcarriers e.g. composed of, or containing gelatin, plastic or glass.

The cells can be grown using a variety of cell culture media or combinations of cell media. Such culture media are for example:

1. Ham's F10 supplemented with 2% of a 2.8% sodium bicarbonate solution, 100 International Units (IU) of Penicillin, 10% phosphate broth, 8% Fetal Calf Serum and 2% chicken serum. (Moscovici et al., Cell 11, page 95–103, 05-1977).
2. Medium 199 with Hanks salt supplemented with 0.3% Tryptose phosphate broth, 0.477% HEPES and 10% Fetal Calf Serum. (Fiorentine et al., Develop. biol. Standard 60, page 421–430, 1985)
3. Eagle's MEM with 10% adult bovine serum and antibiotics (Penicillin 100 iu/ml, Neomycin 100 µg/ml and 100 µg/ml) (Reddy et al., Idian Vet. J. 68, page 907–910, 1991)
4. 44% nutrient mixture F-10 and 56% medium 199, supplemented with 5% tryptose phosphate broth, 10% Fetal Calf Serum, 10 µg/ml Gentamicin, 10 mM HEPES and 0.015% sodium bicarbonate. (Schnitzlein et al., Virus Research 10, page 65–76, 1988)
5 Ham's F12 medium.

Optionally these cell media or combinations of cell media can be supplemented with readily available energy sources (in particular sugars, such as glucose, fructose and/or ribose) and/or with amino acid sources such as proteins (e.g. milk proteins and/or serum proteins).

For the subcultivation of the QT-35 cells it is possible to use proteolytic enzymes such as trypsin and collagenase.

Cells can be frozen in the presence of cryoprotectors, such as Dimethyl sulfoxide (DMSO) or glycerol. Freezing of the cells as well as the cell associated virus can be performed by establishing a gradual decrease in temperature of e.g. 1° C. per minute to the desired storage temperature, which is preferably, the temperature of liquid nitrogen.

The diluent for the vaccine can be any physiological solution, but preferably a phosphate buffered saccharose solution containing NZ-amine.

EXAMPLE 1

Vaccine Production

The starting material for the production run was strain CVI 988 which had been passaged 16 times on QT35 cells. Samples of this virus material after the 16$^{th}$ passage were deposited on Jun. 7, 1995 at the Collection Nationale de Cultures de Microorganismes (CNCM) of the Institut Pasteur (Paris, France) under No. I-1585.

In the production run cells as well as virus were always grown at 39° C. For vaccine production QT35 cells were seeded in roller bottles in a concentration of $8.8 \times 10^4$ cells/cm$^2$ and incubated. After 3 days incubation the roller bottles were inoculated with the passage 16 virus at a multiplicity of infection (m.o.i.) of 0.01. After 4 days incubation the infected cultures were harvested by trypsinization. Per roller bottle $43.1 \times 10^7$ cells were harvested ($8.8 \times 10^5$/cm$^2$).

A sample was titrated and an other sample was used to inoculate (split ratio 1 to 20) roller bottles with monolayers of QT35 cells. These cells were seeded 3 days before in a concentration of $8.8 \times 10^4$ cells/cm$^2$. Three days after inoculation the infected monolayers were harvested by trypsinization. Per roller bottle $58.8 \times 10^7$ cells were harvested ($12.0 \times 10^5$ cells/cm$^2$). The cell suspension was concentrated by centrifugation and diluted in freezing medium to a concentration of $3 \times 10^7$ cells/ml. This cell suspension was filled in 1 ml. vials and frozen in liquid nitrogen. The ampoules were designated as Master Seed Virus (MSV). In total 24 ampoules were frozen in liquid nitrogen. Two ampoules were titrated and the titer appeared to be $10^{6.20}$ TCID$_{50}$/ml.

For working seed virus (WSV) production roller bottles were seeded in a concentration of $8.7 \times 10^4$ cells/cm$^2$ and incubated. The roller bottles were inoculated with Master Seed Virus at a moi of 0.01. After 4 days incubation the infected cultures were harvested by trypsinization. Per bottle $55.4 \times 10^7$ cells were harvested ($11.3 \times 10^5$ cells/cm$^2$).

A sample was titrated and an other sample was used to inoculate (in a ratio of 1:20) monolayers of QT35 cells. These monolayers had been seeded 3 days before in a concentration of $8.7 \times 10^4$ cells/cm$^2$. After 3 days of virus growth the infected monolayers were harvested by trypsinization. Per roller bottle $32.6 \times 10^7$ cells were harvested ($6.65 \times 10^5$ cells/cm$^2$). The cell suspension was concentrated by centrifugation and diluted in freezing medium to a concentration of $3 \times 10^7$ cells/ml. This cell suspension was filled in 1 ml. vials and frozen in liquid nitrogen. A sample was titrated and the titer appeared to be $10^{6.20}$ TCID$_{50}$/ml. These ampoules were designated as Working Seed Virus.

For vaccine production QT35 cells were seeded in roller bottles in a concentration of $8.7 \times 10^5$ cells/cm$^2$. Three days after seeding the roller bottles were inoculated with Working Seed Virus at a moi of 0.01. After 4 days of incubation the infected cultures were harvested by trypsinization. Per bottle $59.6 \times 10^7$ cells were harvested. ($12.2 \times 10^5$ cells/cm$^2$)

A sample was titrated and an other sample was used to inoculate (in a ratio of 1:20) monolayers of QT35 cells. These monolayers had been seeded 3 days before in a concentration of $8.7 \times 10^5$ cells/cm$^2$. After 4 days the infected monolayers were harvested by trypsinization.

A sample was titrated and an other sample was used to inoculate (in a ratio of 1:30) monolayers of QT35 cells. These monolayers had been seeded 3 days before in a concentration of $8.7 \times 10^5$ cells/cm$_2$. After 3 days the infected monolayers were harvested by trypsinization.

The cell suspension was concentrated by centrifugation and diluted in freezing medium to a concentration of $3 \times 10^7$ cells/ml. This cell suspension was filled in 1 ml vials and frozen in liquid nitrogen. A sample was titrated and the titer appeared to be $10^{6.72}$ TCID$_{50}$/ml. These ampoules were designated as vaccine batch passage 23, production date Mar. 13, 1995.

The used passage for vaccination is 23. That is 5 passages from the Master Seed Virus. From 1 vial master seed virus it is possible to produces ±1200 ampoules Working Seed Virus. With 1 ampoule Working Seed Virus we can produce ±37,500 ampoules of vaccines, for vaccinating 37,500,000 chickens.

EXAMPLE 2

Efficacy of a Vaccine Produced from Strain Rispens Adapted on QT35 Cells

The vaccine was tested for efficacy as described in the monograph 589 (1994) of the European Pharmacopoeia for Marek's disease vaccines, with the exception that the chickens were challenged 5 days after vaccination, instead of the 9 days interval prescribed by the monograph. Challenge after 5, rather than after 9 days, makes the test more sensitive. For the passages on QT35 cells Poulvac Marek CVI batch 369 had been used as starting material. Vaccine virus passaged 21 times on QT35 cells according to example 1 was tested.

One-day-old SPF chicks were vaccinated once, each with a regular vaccine dose ($10^{3.0}$ $TCID_{50}$ or higher). Five days after vaccination the birds were challenged with a virulent Marek's disease virus strain. After challenge the birds were examined regularly for symptoms of Marek's disease. Seventy days after challenge all birds were killed and investigated for macroscopic lesions of Marek's disease.

The results of the study are summarized in Table 1.

| vaccine | $TCID_{50}$/1000 doses vial | Chickens with MD/total of chickens | protection index (%) |
|---|---|---|---|
| QT35 vaccine, passage 21 | $10^{6.10}$ | 3/30 | 88 |
| No vaccine | not applicable | 24/28 | not applicable |

These results show that in the non-vaccinated group 86% of the birds have Marek's disease (complies with the European Pharmacopoeia). So, the vaccine produced on QT35 cells complies with the guidelines of the European Pharmacopoeia, which state that the protection index should be at least 80%.

Conclusion: In the above described experiments it is shown that the Marek's disease vaccine produced on QT35 cells is efficacious.

We claim:

1. A method for growing Marek's Disease Virus (MDV) of serotype 1 comprising seeding the Marek's disease virus of serotype 1 onto an avian continuous cell line and incubating under conditions suitable for the reproduction of the virus on the cell line.

2. The method according to claim 1, wherein the avian continuous cell line is a quail cell line.

3. The method according to claim 1, wherein the avian continuous cell line is a QT-35 cell line.

4. The method according to claim 1, wherein the virus is strain I-1585 deposited at the Institute Pasteur (Paris, France).

5. A method for growing Marek's Disease Virus (MDV) of serotype 1 comprising seeding the Marek'disease virus of serotype 1 onto an avian continuous cell line incubating under conditions suitable for the reproduction of the virus on the cell line and mixing the virus with a carrier in an amount effective to form a vaccine.

* * * * *